(12) United States Patent
Galey et al.

(10) Patent No.: US 6,602,869 B1
(45) Date of Patent: Aug. 5, 2003

(54) COMPOUNDS DERIVED FROM BENZOIC ACID ESTERS, COMPOSITION CONTAINING SAID COMPOUNDS AND USE THEREOF

(75) Inventors: Jean-Baptiste Galey, Aulnay (FR); Maria Dalko, Gif sur Yvette (FR); Lionel Breton, Versailles (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/937,654

(22) PCT Filed: Mar. 24, 2000

(86) PCT No.: PCT/FR00/00752

§ 371 (c)(1),
(2), (4) Date: Nov. 21, 2001

(87) PCT Pub. No.: WO00/59866

PCT Pub. Date: Oct. 12, 2000

(30) Foreign Application Priority Data

Apr. 1, 1999 (FR) .............................. 99 04104

(51) Int. Cl.[7] ...................... A61K 31/535; A61K 31/24; A61K 31/235; A01N 37/12; A01N 37/14
(52) U.S. Cl. ..................... 514/239.2; 514/535; 514/538; 514/544; 544/165; 544/172; 560/43; 560/47; 560/49
(58) Field of Search .............................. 560/18, 43, 47, 560/49; 544/165, 172; 514/239.2, 535, 538, 544

(56) References Cited

U.S. PATENT DOCUMENTS

| | | | |
|---|---|---|---|
| 4,139,619 A | 2/1979 | Chidsey, III | 424/45 |
| 4,596,812 A | 6/1986 | Chidsey, III et al. | 514/256 |
| 4,767,750 A | 8/1988 | Jacquet et al. | 514/159 |
| 4,973,474 A | 11/1990 | Hocquaux et al. | 514/272 |
| 5,132,106 A | 7/1992 | Tuloup et al. | 424/70 |
| 5,438,058 A | 8/1995 | Dufetel et al. | 514/252 |
| 5,466,694 A | 11/1995 | Terranova et al. | 514/272 |
| 5,760,043 A | 6/1998 | Dufetel et al. | 514/272 |
| 5,772,990 A | 6/1998 | Hocquaux et al. | 424/70.1 |

FOREIGN PATENT DOCUMENTS

| | | |
|---|---|---|
| EP | 0 353 123 | 1/1990 |
| EP | 0 356 271 | 2/1990 |
| EP | 0 408 442 | 1/1991 |
| EP | 0 420 707 | 4/1991 |
| EP | 0 459 890 | 12/1991 |
| EP | 0 519 819 | 12/1992 |
| EP | 0 522 964 | 1/1993 |
| EP | 0 648 488 | 4/1995 |
| FR | 2 581 542 | 11/1986 |
| JP | 52-128329 | * 10/1977 |
| WO | WO 94/22468 | 10/1994 |
| WO | WO 97/32562 | 9/1997 |

OTHER PUBLICATIONS

Webster's II New Riverside Dictionary. Houghton Mlfflin Co., p. 316 (1994).*
"Anilides of (R)–Trifluoro–2–hydroxy–2–methylpropionic Acid as Inhibitors of Pyruvate Dehydrogenase Kinase" Bebernitz et al, J. Med. Chem. vol. 43, pp. 2248–2257 (2000).*
English abstract of JP 52–128329 (Mori et al) Derwent Information, Ltd. (1999).*
"N.N–Dimethylacetamide (DMAC)" technical leaflet, BASF (2001).*
Frank D. King, "Bioisosteres, Conformational Restriction, and Pro–drugs—Case History: An Example of a Conformational Restriction Approach," Medicinal Chemistry: Principles and Practice, Chapter 14, 1994, pp. 206–225.
Thomas D. Aicher, "(R)–3,3,3–Trifluoro–2–hydroxy–2–methyl–propionamides Are Orally Active Inhibitors of Pyruvate Dehydrogenase Kinase," Journal of Medicinal Chemistry, vol. 42, No. 15, Jul. 1999, pp. 2741–2746.
English language Derwent Abstract of EP 0 353 123, Jan. 31, 1990.
English language Derwent Abstract of EP 0 648 488, Apr. 19, 1995.

* cited by examiner

*Primary Examiner*—Richard L. Raymond
*Assistant Examiner*—Zachary C. Tucker
(74) *Attorney, Agent, or Firm*—Finnegan, Henderson, Farabow, Garrett & Dunner, L.L.P.

(57) ABSTRACT

This invention relates to novel compounds of formula (I) wherein $R_1$ represents a polymer, aryl or alkyl group, $R_2$ represents a hydrogen atom, a halogen atom, a radical CN, $CF_3$, OH, $OCF_3$, COOH, $R^7$, $OR^7$ or $OCOR^7$, $R^3$ represents an aryl or alkyl halogen, $R_4$ represents an alkyl radical. The invention also relates to a cosmetic composition comprising said compounds and to the use thereof to reduce and/or curb hair loss i.e. to increase and/or stimulate the growth of said hair.

37 Claims, No Drawings

COMPOUNDS DERIVED FROM BENZOIC ACID ESTERS, COMPOSITION CONTAINING SAID COMPOUNDS AND USE THEREOF

This application filed under 35 U.S.C. 371, on Nov. 21, 2001, is the U.S. National stage of PCT/FR00/00752, filed Mar. 24, 2000.

The present invention relates to novel derivatives of benzoic acid esters, to their use in particular in cosmetics, and to the compositions containing them.

Inhuman beings, the growth of hair and its renewal are mainly determined by the activity of the hair follicles and their dermoepidermal environment. Their activity is cyclic and comprises essentially three phases, namely the anagen phase, the catagen phase and the telogen phase.

The anagen phase or growth phase, which lasts for several years and during which the hair grows longer, is followed by a very short and transitory catagen phase which lasts for a few weeks, and then by a resting phase, called the telogen phase, which lasts for a few months.

At the end of the resting period, the hair falls out and another cycle begins. The hair is therefore continuously renewed, and of the approximately 150,000 hair strands which make up the hair, at each instant, approximately 10% of them are in the resting phase and will therefore be replaced in a few months.

In a large number of cases, the premature loss of the hair occurs in genetically predisposed subjects and it affects men in particular. It involves more particularly androgenetic or androgenic or alternatively androgeno-genetic alopecia.

This alopecia is essentially due to a disruption in hair renewal which causes, in the first instance, the acceleration of the frequency of the cycles at the expense of the quality of the hair and then of its quantity. A gradual deterioration of the hair is brought about by regression of the so-called <<terminals>> hair at the down stage. Some areas are preferably affected, in particular the temporal or frontal sinuses and the upper part of the occipital in men, whereas in women a diffuse alopecia of the vertex is mainly observed.

Substances which make it possible to suppress or reduce the effect of alopecia, and in particular to induce or stimulate growth of head hair and/or body hair, or even to reduce its loss, have been sought for many years, in particular in the cosmetics industry. For this purpose, a large number of widely varying active substances have indeed already been proposed, such as for example 2,4-diamino-6-piperidinopyrimidine 3-oxide or <<Minoxidil>> described in U.S. Pat. No. 4,596,812 or its many derivatives such as those described for example in patent applications EP 353123, EP 356271, EP 408442, EP 522964, EP 420707, EP 459890 and EP 519819. There may also be mentioned 6-amino-1,2-dihydro-1-hydroxy-2-imino-4-piperidinopyrimidine and its derivatives, which are described more particularly in patent U.S. Pat. No. 4,139,619.

The fact remains, in general, that it would be advantageous and useful to be able to have active compounds other than those already known, which are preferably potentially more active and/or less toxic, and which can be used in the cosmetic field.

However, after many research studies, the Applicant has just demonstrated that novel compounds, derived from benzoic acid esters, exhibit remarkable properties which may justify their use for reducing and/or slowing down the loss of head hair and/or body hair. These compounds could also be potentially capable of inducing and/or stimulating its growth.

Thus, the subject of the invention is novel compounds corresponding to the following formula (I):

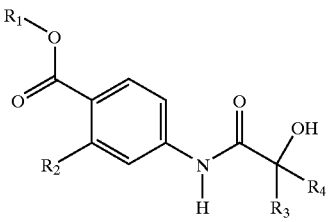

in which:

$R_1$ represents:
  a linear or branched $C_1$–$C_{12}$ aliphatic alkyl group, optionally substituted with one or more groups chosen from OH, $NH_2$, SH; $CONHR^5$, $COOR^5$, $OR^5$, $SR^5$, $SiOR^5$, $NHR^5$ in which $R_5$ is a linear or branched $C_1$–$C_4$ alkyl radical; CN, $CF_3$, halogen, or with one or more aliphatic or aromatic, optionally heterocyclic, $C_3$–$C_6$ rings;
  an aryl group, optionally substituted with one or more groups OH, $NH_2$, SH, COOH; $CONHR^6$, $COOR^6$, $OR^6$, $SR^6$, $NHR^6$ in which $R^6$ is a linear or branched $C_1$–$C_{12}$ alkyl radical; CN, $CF_3$, halogen, or with one or more aliphatic or aromatic, optionally heterocyclic, $C_3$–$C_6$ rings; or
  a natural or synthetic polymer or copolymer carrying one or more combinations of the following groups: hydroxyl, carboxylate, primary amine, secondary amine, tertiary amine, thiol, aldehyde.

$R_2$ represents a hydrogen or halogen atom, a radical CN, $CF_3$, OH, $OCF_3$, COOH, $R^7$, $OR^7$ or $OCOR^7$ in which $R^7$ denotes a linear or branched $C_1$–$C_4$ aliphatic alkyl radical.

$R_3$ represents a mono- or polyhalogenated linear or branched $C_1$–$C_4$ alkyl radical, or an aryl radical, optionally substituted with one or more groups chosen from OH, $NH_2$, SH, CN, $CF_3$, halogen, COOH, $CONHR^8$, $COOR^8$, $OR^8$, $SR^8$, $NHR^8$ in which $R^8$ is a linear or branched $C_1$–$C_{12}$ alkyl radical.

$R_4$ represents a linear or branched $C_1$–$C_4$ alkyl radical, optionally substituted with a halogen atom, or represents a $CF_3$ radical.

The subject of the invention is also a composition, in particular a cosmetic composition, comprising, in a physiologically acceptable medium, at least one compound as defined above.

The subject of the invention is also the use, in particular in a composition, in particular a cosmetic composition, or for the preparation of a physiologically acceptable composition, of at least one compound corresponding to formula (I) for reducing and/or slowing down the loss of head hair and/or body hair, or even inducing and/or stimulating its growth.

One of the advantages of the invention consists in the fact that the compounds according to the invention are free of side effects since they are metabolized into an acid which is free of anti-androgen effect.

The compounds according to the invention are represented by the following formula (I):

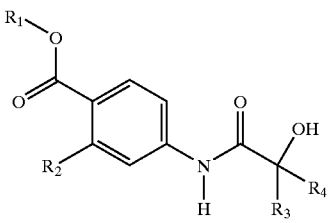

in which:
R₁ represents:
a linear or branched $C_1$–$C_{12}$ aliphatic alkyl group, optionally substituted with one or more groups chosen from OH, $NH_2$, SH; $CONHR^5$, $COOR^5$, $OR^5$, $SR^5$, $SiOR^5$, $NHR^5$ in which $R^5$ is a linear or branched $C_1$–$C_4$ alkyl radical; CN, $CF_3$, halogen, or with one or more aliphatic or aromatic, optionally heterocyclic, $C_3$–$C_6$ rings;
an aryl group, optionally substituted with one or more groups OH, $NH_2$, SH, COOH; $CONHR^6$, $COOR^6$, $OR^6$, $SR^6$, $NHR^6$ in which $R^6$ is a linear or branched $C_1$–$C_{12}$ alkyl radical; CN, $CF_3$, halogen, or with one or more aliphatic or aromatic, optionally heterocyclic, $C_3$–$C_6$ rings; or
a natural or synthetic polymer or copolymer carrying one or more combinations of the following groups: hydroxyl, carboxylate, primary amine, secondary amine, tertiary amine, thiol, aldehyde.
$R_2$ represents a hydrogen or halogen atom, a radical CN, $CF_3$, OH, $OCF_3$, COOH, $R^7$, $OR^7$ or $OCOR^7$ in which $R^7$ denotes a linear or branched $C_1$–$C_4$ aliphatic alkyl radical.
$R_3$ represents a mono- or polyhalogenated linear or branched $C_1$–$C_4$ alkyl radical, or an aryl radical, optionally substituted with one or more groups chosen from OH, $NH_2$, SH, CN, $CF_3$, halogen, COOH, $CONHR^8$, $COOR^8$, $OR^8$, $SR^8$, $NHR^8$ in which $R^8$ is a linear or branched $C_1$–$C_{12}$ alkyl radical.
$R_4$ represents a linear or branched $C_1$–$C_4$ alkyl radical, optionally substituted with a halogen atom, or represents a $CF_3$ radical.

Among the natural polymers which may be to represent $R_1$, there may be mentioned modified natural polymers such as ether or ester derivatives of cellulose, polysaccharides, oligosaccharides and glycosaminoglucans.

Preferably, $R_1$ represents an optionally substituted aryl group, and in particular a phenyl or benzyl group.

Preferably, $R_2$ represents a hydrogen atom, a halogen atom and in particular a chlorine atom, or a hydroxyl radical.

Preferably, $R_3$ represents a halogenated, in particular fluorinated, alkyl radical, or a phenyl radical. In particular, $R_3$ may represent the $CF_3$ radical.

Preferably, $R_4$ represents a methyl radical.

Among the compounds of formula (I), there may be more particularly mentioned:
4-(O-methyloxime)phenyl ester of 2-hydroxy-4-(3,3,3-trifluoro-2-hydroxy-2-methylpropionylamino)benzoic acid;
phenyl ester of 2-hydroxy-4-(3,3,3-trifluoro-2-hydroxy-2-methylpropionylamino)benzoic acid;
methyl ester of 4-(3,3,3-trifluoro-2-hydroxy-2-methylpropionylamino)benzoic acid;
para-tolyl ester of 2-hydroxy-4-(3,3,3-trifluoro-2-hydroxy-2-methylpropionylamino)benzoic acid;
phenyl ester of 2-hydroxy-4-(2-phenyl-2-hydroxypropionylamino)benzoic acid;
methyl ester of 2-methoxy-4-(3,3,3-trifluoro-2-hydroxy-2-methylpropionylamino)benzoic acid;
phenyl ester of 2-chloro-4-(3,3,3-trifluoro-2-hydroxy-2-methylpropionylamino)benzoic acid;
methyl ester of 2-ethyl-4-(3,3,3-trifluoro-2-hydroxy-2-methylpropionylamino)benzoic acid;
3,5-bis(trifluoromethyl)benzyl ester of 2-hydroxy-4-(3,3,3-trifluoro-2-hydroxy-2-methylpropionylamino)benzoic acid;
tert-butyl ester of 2-hydroxy-4-(3,3,3-trifluoro-2-hydroxy-2-methylpropionylamino)benzoic acid;
3-morpholinopropyl ester of 2-hydroxy-4-(3,3,3-trifluoro-2-hydroxy-2-methylpropionylamino)benzoic acid;
4-octylphenyl ester of 2-hydroxy-4-(3,3,3-trifluoro-2-hydroxy-2-methylpropionylamino)benzoic acid; and
methyl ester of 2-hydroxy-4-(3,3,3-trifluoro-2-hydroxy-2-methylpropionylamino)benzoic acid.

The compounds of formula (I) may be used alone or in the form of a mixture.

The quantity of compound to be used in the compositions according to the invention can be easily determined by persons skilled in the art according to the nature of the compound used, the person to be treated and/or the desired effect. In general, this quantity may be between 0.0001 and 30% by weight relative to the total weight of the composition, in particular between 0.01 and 10% by weight, and preferably between 0.1 and 5% by weight.

Thus, the compounds of formula (I) according to the invention may in particular be used in a composition or for the preparation of a composition which comprises, moreover, a physiologically acceptable medium.

This composition may be provided in the form of a cosmetic composition which therefore comprises a cosmetically acceptable medium.

The physiologically acceptable medium in which the compounds according to the invention may be used can be easily determined by persons skilled in the art.

In general, it may be anhydrous or aqueous.

The expression anhydrous medium is understood to mean a solvent medium containing less than 1% by weight of water. This medium may consist of an organic. solvent or of a mixture of organic solvents chosen more particularly from $C_1$–$C_4$ alcohols such as ethanol; alkylene glycols such as propylene glycol; alkyl ethers of alkylene glycols or of dialkylene glycols, in which the alkyl or alkylene radicals contain from 1 to 4 carbon atoms.

The expression aqueous medium is understood to mean a medium consisting of water or of a mixture of water and of another physiologically acceptable solvent, chosen in particular from the organic solvents mentioned above. In the latter case, these other solvents may represent about 5 to 95% by weight of the composition.

It is possible to add to the composition, in combination with the compounds of the invention, one or more compounds which further enhance the activity on hair regrowth and/or on slowing down hair loss, and which have already been described for this activity.

There may be mentioned more particularly, without limitation:
nicotinic acid esters, including in particular tocopherol nicotinate, benzyl nicotinate and $C_1$–$C_6$ alkyl nicotinates such as methyl or hexyl nicotinates;
pyrimidine derivatives, such as 2,4-diamino-6-piperidinopyrimidine 3-oxide or <<Minoxidil>> described in patents U.S. Pat. Nos. 4,139,619 and 4,596,812;
agents promoting hair regrowth such as those described in patent application EP0648488;

antibacterial agents such as macrolides, pyranosides and tetracyclines, and in particular erythromycin;

calcium-antagonizing agents such as cinnarizin, diltiazem, nimodipine and nifedipine;

hormones such as estriol and its analogs, or thyroxin and its salts;

steroidal or nonsteroidal anti-inflammatory agents, such as corticosteroids (for example: hydrocortisone);

antiandrogenic agents such as oxendolone, spironolactone, diethylstilbestrol and flutamide;

steroidal or nonsteroidal inhibitors of 5-α-reductases such as finasteride;

potassium agonists such as cromakalim and nicorandil;

agonists of retinoid RXR receptors and antagonists of retinoids;

scavengers of OH radicals, such as dimethyl sulfoxide;

peptides such as for example the tripeptide Lys-Pro-Val, and more generally α-MSH and its derivatives.

The following compounds may also be added to this list:

diazoxide, spiroxasone, phospholipids such as lecithin, linoleic and linolenic acids, salicylic acid and its derivatives described in French patent FR 2 581 542, such as their salicylic acid derivatives carrying an alkanoyl group having from 2 to 12 carbon atoms at the 5-position of the benzene ring, hydroxycarboxylic or ketocarboxylic acids and their esters, lactones and their corresponding salts, anthralin, carotenoids, eicosatetraenoic and eicosatrienoic acids or their esters and amides, vitamin D and its derivatives, extracts of plant or bacteria origin.

Moreover, there may be added, to the physiologically acceptable medium, adjuvants normally used in the field of application considered, in particular in the cosmetic field, such as surfactants, thickening or gelling agents, cosmetic agents, preservatives, alkalinizing or acidifying agents well known in the state of the art.

The nature and the quantity of these adjuvants may be chosen by persons skilled in the art on the basis of their general knowledge so as to obtain the form of presentation desired for the composition. In any case, persons skilled in the art will be careful to choose all the possible additional compounds and/or their quantity so that the advantageous properties of the composition according to the invention are not, or not substantially, impaired by the addition envisaged.

The compositions according to the invention may be provided in the form of a lotion which is thickened to a greater or lesser degree, a gel, an emulsion or a cream. They may be optionally used in pressurized form as an aerosol or as a spray from a pump dispenser.

The compositions may also be provided in liposomal form, as described in particular in patent application WO 94/22468. In this case, the compound encapsulated in the liposomes may be selectively delivered to the hair follicles.

The compositions according to the invention may be applied to the alopecic areas of the scalp and/or of the head hair and/or of the body hair of one individual, and may then be optionally left in contact for several hours and may be optionally rinsed off.

It is possible, for example, to apply the composition comprising an effective quantity of a compound according to the invention to the hair or the scalp in the evening, to keep it in contact overnight and to optionally shampoo in the morning. These applications may be repeated daily for one or more months according to the individual.

Thus, the subject of the present invention is also a method for the cosmetic treatment of head hair, body hair and/or the scalp, in which a cosmetic composition comprising an effective quantity of at least one compound of formula (I) is applied to the head hair, the body hair and/or the scalp, leaving it in contact with the head hair and/or the scalp and/or the body hair, and optionally rinsing off.

The method of treatment exhibits the characteristics of a cosmetic method insofar as it makes it possible to improve the esthetic appearance of the hair by giving it greater vitality and improved appearance.

The invention is illustrated in greater detail in the following examples.

EXAMPLE 1

Preparation of the Phenyl Ester of 2-hydroxy-4-(3,3,3-trifluoro-2-hydroxy-2-methylpropionylamino) Benzoic Acid

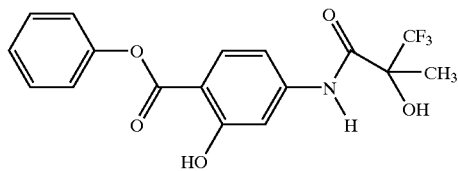

2.1 g of 3,3,3-trifluoro-2-hydroxy-2-methylpropanoic acid are solubilized in 20 ml of anhydrous N,N-dimethylacetamide. The medium is cooled to −20° C. and then 1 ml of thionyl chloride is added dropwise. The reaction medium is stirred for 1 hour at −20° C. and then 2.0 g of phenyl 4-aminosalicylate are added. The temperature is allowed to rise to about 25° C. and the mixture is stirred for one night (12 hours). The mixture is poured into 100 ml of ice-cold water and extracted 3 times with 50 ml of dichloromethane.

The organic phase is washed with water and then dried over $Na_2SO_4$ and evaporated to dryness.

A yellow oil is obtained which is purified by chromatography on a silica column (eluent: dichloromethane). The oil obtained after evaporating to dryness is taken up in 20 ml of a heptane/toluene 1:1 mixture.

A white solid is obtained which is recrystallized from 10 ml of toluene and dried under vacuum.

1.35 g of phenyl ester of 2-hydroxy-4-(3,3,3-trifluoro-2-hydroxy-2-methylpropionylamino)benzoic acid are obtained (yield=50%).

$C_{17} H_{14} F_3 NO_5$ MW=369

NMR spectrum: $^1$H (400 MHz) in $CDCl_3$: conforms with the expected structure

Elemental analysis

|  | C | H | N | F |
|---|---|---|---|---|
| % calculated | 55.28 | 3.79 | 3.79 | 15.45 |
| % found | 55.23 | 3.73 | 3.85 | 15.71 |

EXAMPLE 2

The following compounds are prepared in the same manner as in example 1:

(a) methyl ester of 4-(3,3,3-trifluoro-2-hydroxy-2-methylpropionylamino)benzoic acid of formula:

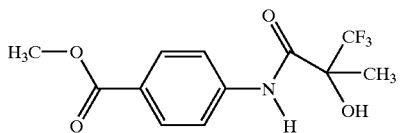

NMR spectrum: ¹H (500 MHz) in DMSO: conforms with the expected structure (b) para-tolyl ester of 2-hydroxy-4-(3,3,3-trifluoro-2-hydroxy-2-methylpropionylamino)benzoic acid of formula:

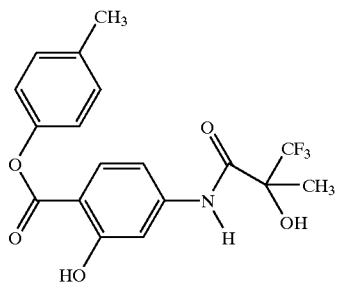

NMR spectrum: ¹H (500 MHz) in DMSO: conforms with the expected structure (c) phenyl ester of 2-hydroxy-4-(2-phenyl-2-hydroxypropionylamino)benzoic acid of formula:

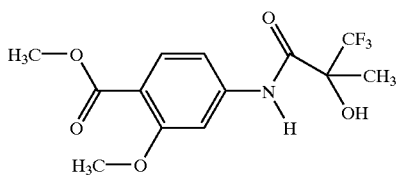

(d) methyl ester of 2-methoxy-4-(3,3,3-trifluoro-2-hydroxy-2-methylpropionylamino)benzoic acid of formula:

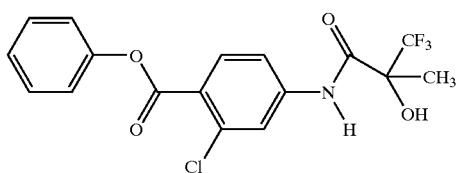

(e) phenyl ester of 2-chloro-4-(3,3,3-trifluoro-2-hydroxy-2-methylpropionylamino)benzoic acid of formula:

(f) methyl ester of 2-ethyl-4-(3,3,3-trifluoro-2-hydroxy-2-methylpropionylamino)benzoic acid of formula:

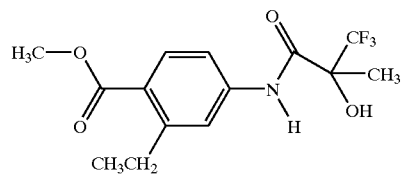

(g) 3,5-bis(trifluoromethyl)benzyl ester of 2-hydroxy-4-(3,3,3-trifluoro-2-hydroxy-2-methylpropionylamino)benzoic acid of formula:

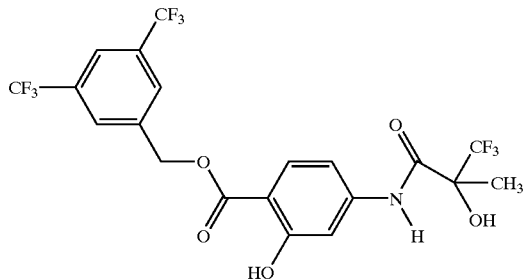

(h) tert-butyl ester of 2-hydroxy-4-(3,3,3-trifluoro-2-hydroxy-2-methylpropionylamino)benzoic acid of formula:

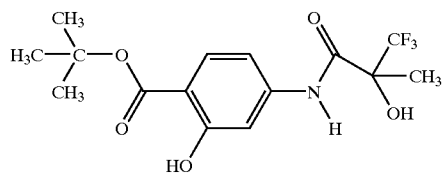

(i) 3-morpholinopropyl ester of 2-hydroxy-4-(3,3,3-trifluoro-2-hydroxy-2-methylpropionylamino)benzoic acid of formula:

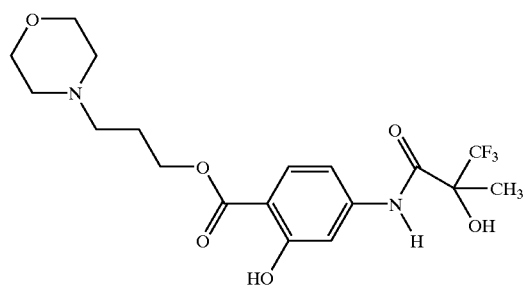

(j) 4-octylphenyl ester of 2-hydroxy-4-(3,3,3-trifluoro-2-hydroxy-2-methylpropionylamino)benzoic acid of formula:

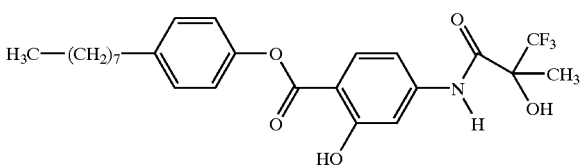

(k) 4-(O-methyloxime)phenyl ester of 2-hydroxy-4-(3,3,3-trifluoro-2-hydroxy-2-methylpropionylamino)benzoic acid of formula:

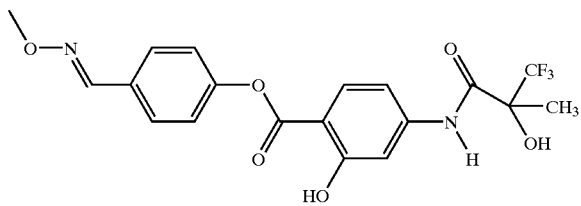

(l) methyl ester of 2-hydroxy-4-(3,3,3-trifluoro-2-hydroxy-2-methylpropionylamino)benzoic acid of formula:

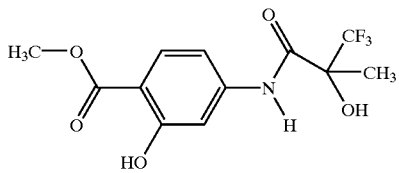

NMR spectrum: $^1$H (500 MHz) in DMSO: conforms with the expected structure

EXAMPLE 3

Daily Lotion

A composition comprising the following constituents is prepared:

| | |
|---|---|
| compound of example 1 | 1 g |
| ethanol | 30 g |
| perfume, colorants | qs |
| demineralized water | qs 100 g |

EXAMPLE 4

Liposome-based Gel

A composition comprising the following constituents is prepared:

| | |
|---|---|
| compound of example 2(a) | 0.5 g |
| carbomer | 0.25 g |
| triethanolamine | qs pH = 7 |
| preservatives | qs |
| demineralized water | qs 100 g |

EXAMPLE 5

Anti-hair Loss Lotion

A composition comprising the following constituents is prepared:

| | |
|---|---|
| compound of example 2(b) | 1 g |
| propylene glycol | 10 g |
| isopropanol | qs 100 g |

1 ml of this lotion is applied to the scalp, at the rate of once to twice per day.

EXAMPLE 6

Anti-hair Loss Lotion

A composition comprising the following constituents is prepared:

| | |
|---|---|
| compound of example 2(c) | 2 g |
| propylene glycol | 30 g |
| ethanol | 40.5 g |
| water | qs 100 g |

This lotion is applied to the scalp, once or twice per day, in an amount of 1 ml per application.

EXAMPLE 7

Anti-hair Loss Lotion

A composition comprising the following constituents is prepared:

| | |
|---|---|
| compound of example 2(d) | 1 g |
| propylene glycol monomethyl ether (Dowanol PM from Dow) | 20 g |
| hydroxypropyl cellulose (Klucel G from Hercules) | 3 g |
| ethanol | 40 g |
| water | qs 100 g |

This thickened lotion is applied to the scalp, once or twice per day, in an amount of 1 ml per application.

With each of the compositions described in examples 3 to 7 above, a slowing down of hair loss is observed after several months of treatment and depending on the subjects treated.

What is claimed is:

1. A compound of formula (I):

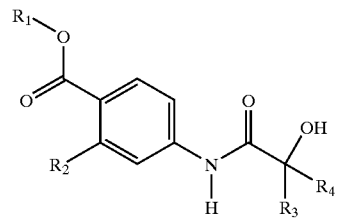

wherein:

$R_1$ is chosen from substituted aryl groups;

$R_2$ is chosen from a hydrogen atom, a halogen atom, $CF_3$, OH, $OCF_3$, COOH, $R^7$, $OR^7$, and $OCOR^7$, wherein $R^7$ is chosen from linear and branched ($C_1$–$C_4$) aliphatic alkyl groups;

$R_3$ is chosen from monohalogenated and polyhalogenated linear and branched ($C_1$–$C_4$) alkyl groups, and from aryl groups; and $R_4$ is chosen from linear and branched ($C_1$–$C_4$) alkyl groups, and a $CF_3$ group.

2. The compound according to claim 1, wherein the aryl groups of $R_1$ are substituted with at least one group chosen from OH, $NH_2$, SH, COOH, $CONHR^6$, $COOR^6$, $OR^6$, $SR^6$, $NHR^6$, aliphatic ($C_3$–$C_6$) rings, aromatic ($C_3$–$C_6$) rings, CN, $CF_3$, and halogen, wherein $R^6$ is chosen from linear and branched ($C_1$–$C_{12}$) alkyl groups.

3. The compound according to claim 2, wherein the aliphatic ($C_3$–$C_6$) rings are heterocyclic.

4. The compound according to claim 2, wherein the aromatic ($C_3$–$C_6$) rings are heterocyclic.

5. The compound according to claim 1, wherein the aryl groups of $R_3$ are substituted with at least one group chosen from OH, $NH_2$, SH, CN, $CF_3$, halogen, COOH, $CONHR^8$, $COOR^8$, $OR^8$, $SR^8$, and $NHR^8$, wherein $R^8$ is chosen from linear and branched ($C_1$–$C_{12}$) alkyl radicals.

6. The compound according to claim 1, wherein the linear and branched ($C_1$–$C_4$) alkyl groups of $R_4$ are substituted with a halogen atom.

7. The compound according to claim 1, wherein the substituted aryl groups are substituted with at least one group chosen from a phenyl group and a benzyl group.

8. The compound according to claim 1, wherein $R_2$ is chosen from a hydrogen atom, a halogen atom, and a hydroxyl group.

9. The compound according to claim 8, wherein the halogen atom is a chlorine atom.

10. The compound according to claim 1, wherein $R_3$ is chosen from a halogenated alkyl group and a phenyl group.

11. The compound according to claim 10, wherein the halogenated alkyl group is fluorinated.

12. The compound according to claim 11, wherein the halogenated alkyl group is a $CF_3$ group.

13. The compound according to claim 1, wherein $R_4$ is a methyl group.

14. A compound of formula (I):

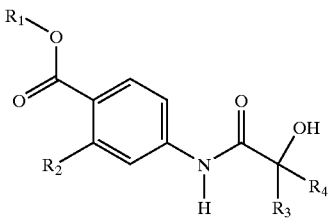

(I)

said compound comprising at least one compound chosen from:
4-(O-methyloxime)phenyl ester of 2-hydroxy-4-(3,3,3-trifluoro-2-hydroxy-2-methylpropionylamino)benzoic acid;
phenyl ester of 2-hydroxy-4-(3,3,3-trifluoro-2-hydroxy-2-methylpropionylamino)benzoic acid;
methyl ester of 4-(3,3,3-trifluoro-2-hydroxy-2-methylpropionylamino)benzoic acid;
para-tolyl ester of 2-hydroxy-4-(3,3,3-trifluoro-2-hydroxy-2-methylpropionylamino)benzoic acid;
phenyl ester of 2-hydroxy-4-(2-phenyl-2-hydroxypropionylamino)benzoic acid;
methyl ester of 2-methoxy-4-(3,3,3-trifluoro-2-hydroxy-2-methylpropionylamino)benzoic acid;
phenyl ester of 2-chloro-4-(3,3,3-trifluoro-2-hydroxy-2-methylpropionylamino)benzoic acid;
methyl ester of 2-ethyl-4-(3,3,3-trifluoro-2-hydroxy-2-methylpropionylamino)benzoic acid;
3,5-bis(trifluoromethyl)benzyl ester of 2-hydroxy-4-(3,3,3-trifluoro-2-hydroxy-2-methylpropionyl-amino)benzoic acid;
tert-butyl ester of 2-hydroxy-4-(3,3,3-trifluoro-2-hydroxy-2-methylpropionylamino)benzoic acid;
3-morpholinopropyl ester of 2-hydroxy-4-(3,3,3-trifluoro-2-hydroxy-2-methylpropionylamino)benzoic acid;
4-octylphenyl ester of 2-hydroxy-4-(3,3,3-trifluoro-2-hydroxy-2-methylpropionylamino)benzoic acid; and
methyl ester of 2-hydroxy-4-(3,3,3-trifluoro-2-hydroxy-2-methylpropionylamino)benzoic acid.

15. A composition comprising, in a physiologically acceptable medium, at least one compound of formula (I):

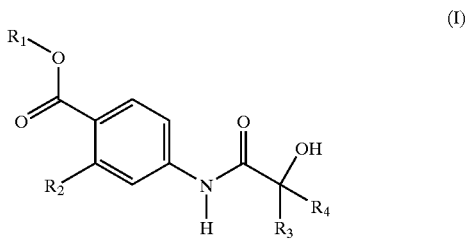

(I)

wherein:

$R_1$ is chosen from substituted aryl groups;

$R_2$ is chosen from a hydrogen atom, a halogen atom, $CF_3$, OH, $OCF_3$, COOH, $R^7$, $OR^7$, and $OCOR^7$, wherein $R^7$ is chosen from linear and branched ($C_1$–$C_4$) aliphatic alkyl groups;

$R_3$ is chosen from monohalogenated and polyhalogenated linear and branched ($C_1$–$C_4$) alkyl groups, and from aryl groups; and $R_4$ is chosen from linear and branched ($C_1$–$C_4$) alkyl groups, and a $CF_3$ group.

16. The composition according to claim 15, wherein the aryl groups of $R_1$ are substituted with at least one group chosen from OH, $NH_2$, SH, COOH, $CONHR^6$, $COOR^6$, $OR^6$, $SR^6$, $NHR^6$, aliphatic ($C_3$–$C_6$) rings, aromatic ($C_3$–$C_6$) rings, CN, $CF_3$, and halogen, wherein $R^6$ is chosen from linear and branched ($C_1$–$C_{12}$) alkyl groups.

17. The composition according to claim 16, wherein the aliphatic ($C_3$–$C_6$) rings are heterocyclic.

18. The composition according to claim 16, wherein the aromatic ($C_3$–$C_6$) rings are heterocyclic.

19. The composition according to claim 15, wherein the aryl groups of $R_3$ are substituted with at least one group chosen from OH, $NH_2$, SH, CN, $CF_3$, halogen, COOH, $CONHR^8$, $COOR^8$, $OR^8$, $SR^8$, and $NHR^8$, wherein $R^8$ is chosen from linear and branched ($C_1$–$C_{12}$) alkyl radicals.

20. The composition according to claim 15, wherein said compound of formula (I) is present in an amount ranging from 0.0001 to 30% by weight relative to the total weight of the composition.

21. The composition according to claim 20, wherein said compound of formula (I) is present in an amount ranging from 0.01 to 10% by weight relative to the total weight of the composition.

22. The composition according to claim 21, wherein said compound of formula (I) is present in an amount ranging from 0.1 to 5.0% by weight relative to the total weight of the composition.

23. The composition according to claim 15, further comprising at least one compound having at least one property chosen from an enhancing activity on hair regrowth and a slowing down of hair loss.

24. The composition according to claim 15, wherein the composition is in a form chosen from a lotion which is thickened, a gel, an emulsion, a cream, and a liposomal form.

25. A cosmetic composition comprising, in a cosmetically acceptable medium, at least one compound of formula (I):

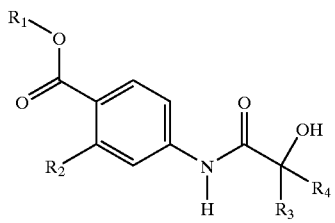

(I)

wherein:

R₁ is chosen from substituted aryl groups;

R₂ is chosen from a hydrogen atom, a halogen atom, $CF_3$, OH, $OCF_3$, COOH, $R^7$, $OR^7$, and $OCOR^7$, wherein $R^7$ is chosen from linear and branched ($C_1$–$C_4$) aliphatic alkyl groups;

R₃ is chosen from monohalogenated and polyhalogenated linear and branched ($C_1$–$C_4$) alkyl groups, and from aryl groups; and R₄ is chosen from linear and branched ($C_1$–$C_4$) alkyl groups, and a $CF_3$ group.

26. The cosmetic composition according to claim 25, wherein the aryl groups of R₁ are substituted with at least one group chosen from OH, $NH_2$, SH, COOH, $CONHR^6$, $COOR^6$, $OR^6$, $SR^6$, $NHR^6$, aliphatic ($C_3$–$C_6$) rings, aromatic ($C_3$–$C_6$) rings, CN, $CF_3$, and halogen, wherein $R^6$ is chosen from linear and branched ($C_1$–$C_{12}$) alkyl groups.

27. The cosmetic composition according to claim 25, wherein the aliphatic ($C_3$–$C_6$) rings are heterocyclic.

28. The cosmetic composition according to claim 25, wherein the aromatic ($C_3$–$C_6$) rings are heterocyclic.

29. The cosmetic composition according to claim 25, wherein the aryl groups of R₃ are substituted with at least one group chosen from OH, $NH_2$, SH, CN, $CF_3$, halogen, COOH, $CONHR^8$, $COOR^8$, $OR^8$, $SR^8$, and $NHR^8$, wherein $R^8$ is chosen from linear and branched ($C_1$–$C_{12}$) alkyl radicals.

30. The cosmetic composition according to claim 25, wherein said compound of formula (I) is present in an amount ranging from 0.0001 to 30% by weight relative to the total weight of the composition.

31. The cosmetic composition according to claim 30, wherein said compound of formula (I) is present in an amount ranging from 0.01 to 10% by weight relative to the total weight of the composition.

32. The cosmetic composition according to claim 31, wherein said compound of formula (I) is present in an amount ranging from 0.1 to 5.0% by weight relative to the total weight of the composition.

33. The cosmetic composition according to claim 25, further comprising at least one compound having at least one property chosen from an enhancing activity on hair regrowth and a slowing down of hair loss.

34. The cosmetic composition according to claim 25, wherein the composition is in a form chosen from a lotion which is thickened, a gel, an emulsion, a cream, and a liposomal form.

35. A method for achieving at least one result chosen from reducing or slowing down loss of head hair and body hair, and inducing or stimulating growth of head hair and body hair, comprising, applying to at least one type of hair chosen from head hair and body hair a composition comprising at least one compound of formula (I):

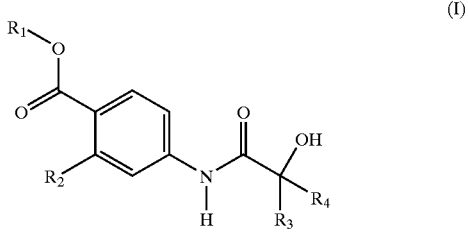

(I)

wherein:

R₁ is chosen from substituted aryl groups;

R₂ is chosen from a hydrogen atom, a halogen atom, $CF_3$, OH, $OCF_3$, COOH, $R^7$, $OR^7$, and $OCOR^7$, wherein $R^7$ is chosen from linear and branched ($C_1$–$C_4$) aliphatic alkyl groups;

R₃ is chosen from monohalogenated and polyhalogenated linear and branched ($C_1$–$C_4$) alkyl groups, and from aryl groups; and R₄ is chosen from linear and branched ($C_1$–$C_4$) alkyl groups, and a $CF_3$ group.

36. The method according to claim 35, wherein the composition is a cosmetic composition.

37. A method for cosmetically treating at least one of head hair, body hair, and the scalp, comprising:

applying to at least one of head hair, body hair, and the scalp, a cosmetic composition comprising, in a physiologically acceptable medium, at least one compound of formula (I):

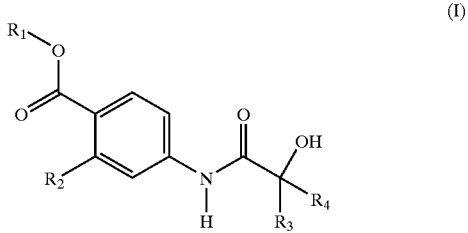

(I)

wherein:

R₁ is chosen from substituted aryl groups;

R₂ is chosen from a hydrogen atom, a halogen atom, $CF_3$, OH, $OCF_3$, COOH, $R^7$, $OR^7$, and $OCOR^7$, wherein $R^7$ is chosen from linear and branched ($C_1$–$C_4$) aliphatic alkyl groups;

R₃ is chosen from monohalogenated and polyhalogenated linear and branched ($C_1$–$C_4$) alkyl groups, and from aryl groups; and R₄ is chosen from linear and branched ($C_1$–$C_4$) alkyl groups, and a $CF_3$ group;

leaving the cosmetic composition in contact with the at least one of head hair, the scalp, and the body hair for a cosmetically effective amount of time, and rinsing the at least one of head hair, the scalp, and the body hair.

* * * * *